United States Patent
Tengku Adnan et al.

(10) Patent No.: US 11,058,737 B2
(45) Date of Patent: Jul. 13, 2021

(54) **USE OF *EUYCOMA LONGIFOLIA* EXTRACT IN ALLEVIATING SYMPTOMS AND/OR CONDITIONS ASSOCIATED WITH HORMONAL IMBALANCE IN FEMALES**

(71) Applicant: BIOTROPiCS MALAYSIA BERHAD, Shah Alam (MY)

(72) Inventors: Tengku Shahrir Tengku Adnan, Cheras (MY); Annie George, Puchong (MY); Sasikala M. Chinnappan, Puchong (MY)

(73) Assignee: BIOTROPICS MALAYSIA BERHAD, Shah Alam (MY)

( * ) Notice: Subject to any disclaimer, the term of this patent is extended or adjusted under 35 U.S.C. 154(b) by 0 days.

(21) Appl. No.: 16/653,092

(22) Filed: Oct. 15, 2019

(65) Prior Publication Data

US 2020/0129573 A1  Apr. 30, 2020

Related U.S. Application Data

(60) Provisional application No. 62/751,881, filed on Oct. 29, 2018.

(51) Int. Cl.
| | | |
|---|---|---|
| *A61K 36/185* | (2006.01) | |
| *A61P 5/08* | (2006.01) | |
| *A61P 5/30* | (2006.01) | |
| *A61P 5/34* | (2006.01) | |

(52) U.S. Cl.
CPC .............. *A61K 36/185* (2013.01); *A61P 5/08* (2018.01); *A61P 5/30* (2018.01); *A61P 5/34* (2018.01)

(58) Field of Classification Search
None
See application file for complete search history.

(56) References Cited

U.S. PATENT DOCUMENTS

| | | | | |
|---|---|---|---|---|
| 2001/0046524 A1* | 11/2001 | Ong | ............... | A61P 5/26 424/769 |
| 2004/0253326 A1* | 12/2004 | Mesko | ............... | A61K 31/37 424/725 |
| 2007/0009621 A1* | 1/2007 | Eng | ............... | A61K 36/185 424/773 |
| 2009/0092687 A1* | 4/2009 | Stein | ............... | A61K 31/56 424/728 |

FOREIGN PATENT DOCUMENTS

| | | |
|---|---|---|
| CN | 104666373 A | 6/2015 |
| EP | 1952816 A1 | 8/2008 |
| MY | 134867 A | 12/2007 |
| MY | 142166 A | 10/2010 |
| MY | 146000 A | 6/2012 |

OTHER PUBLICATIONS

George et al. (2018) Food and Nutrition Research 62: 1374 (16 pages). (Year: 2018).*
Ismail et al. (2012) Evidence-based Complementary and Alternative Medicine, vol. 2012. Article ID 429268 (10 pages) (Year: 2012).*
Udani et al. (2014) Evidence-Based Complementary and Alternative Medicine, vol. 2014, Article ID 179529 (10 pages). (Year: 2014).*
Rehman et al. (2016) Molecules 21,331 (31 pages) (Year: 2016).*
Tambi et al. (2012) Andrologia 44: 226-230. (Year: 2012).*
Talbott et al. (2013) J. Intern. Soc. Sports Nutrition 10: 28 (7 pages) (Year: 2013).*

* cited by examiner

*Primary Examiner* — Russell G Fiebig
(74) *Attorney, Agent, or Firm* — FisherBroyles LLP; Kevin D. Jablonski

(57) ABSTRACT

The present invention is directed to a new kind of medicinal value or health care function of *Eurycoma longifolia* extracts, particularly in the treatment or alleviation symptoms and/or conditions associated to hormonal imbalance in females, including menopause and its related symptoms. In one aspect, the present invention discloses the use of a composition comprising a therapeutically effective amount of *Eurycoma longifolia* extract in the manufacture of a medicament for the alleviation of symptoms and/or conditions associated to hormonal imbalance in females, including menopause and its related symptoms. The alleviation of the symptoms and/or conditions according to the present invention is characterised by inducing a change in the hormonal contents of estrogen, progesterone, follicle stimulating hormone (FSH) and luteinizing hormone (LH). Also disclosed is the use of a pharmaceutical composition comprising the therapeutically effective amount of *Eurycoma longifolia* extract.

9 Claims, No Drawings

USE OF *EUYCOMA LONGIFOLIA* EXTRACT IN ALLEVIATING SYMPTOMS AND/OR CONDITIONS ASSOCIATED WITH HORMONAL IMBALANCE IN FEMALES

FIELD OF THE INVENTION

The present invention relates generally to the medicinal use of *Eurycoma longifolia* extract. More particularly, the present invention relates to the use of *Eurycoma longifolia* extract in alleviating symptoms and/or conditions associated with hormonal imbalance in females.

BACKGROUND OF THE INVENTION

The ovary (female gonad), is one of a pair of reproductive glands in women. They are located in the pelvis, one on each side of the uterus. Each ovary is about the size and shape of an almond. The ovaries are the main source of female hormones, which control the development of female body characteristics such as the breasts, body shape, and body hair. The hormones also regulate the menstrual cycle and pregnancy. Peri-menopause, which is also known as pre-menopause, refers to the period prior to menopause during which normal ovulation cycles gradually give way to cessation of menses. Peri-menopause is often used to refer to the menopausal transitional period. It is not officially a medical term, but is sometimes used to explain certain aspects of the menopause transition in lay terms.

The ovaries produce eggs (ova) and female hormones such as estradiol ($E_2$) and progesterone. $E_2$ is an estrogen steroid hormone and the major female sex hormone. Estrogen helps to regulate parts of the brain that prepare body for sexual and reproductive development. Estrogen stimulates maturation of the ovaries, vagina, uterus and development of breast. Estrogen also helps to preserve bone density and starts of a woman's menstrual cycle. Progesterone plays an important role in regulating the condition of the endometrium of the uterus. Progesterone prepares the uterine lining to receive and nourish a fertilized egg. Progesterone helps to maintain pregnancy and encourages growth of milk gland in the breast. Low progesterone level causes mood swings and irregular cycle. An imbalance of these hormones can lead to symptoms classically associated with aging, such as poor sleep, moody swings and foggy thinking. such as heavy, irregular or painful periods (menstruation), osteoporosis (weak and brittle bones), hot flushes and night sweat, vaginal dryness, reduced sex drive, breast tenderness, infertility, mood swings, stress and long term fatigue. Follicle stimulating hormone (FSH) is produced by the pituitary gland. The main function of FSH is to regulate both ovaries in women. FSH is an established indirect marker of follicular activity. An increase in FSH in women may indicate a reduction in the production of quality eggs and embryos for fertilization. Luteinizing hormone (LH) is produced by gonadotropics cells in the pituitary gland. In women, LH works with FSH to regulate menstrual cycle. LH triggers ovulation process and higher than normal level of LH indicates deteriorating function of ovary.

Fluctuation in hormone levels or mainly known as hormonal imbalance happens when the hormones shift from normal level. Hormonal imbalance in female causes negative impact on weight, mood, sexual desire and fertility. Often it is caused by chronic stress, poor glycaemia control, being overweight, poor nutrition and ageing, which is characteristic of peri- and pre-menopausal women. In women who are pre-menopausal, lower levels of estrogen is produced. In order to compensate low estrogen levels, the body converts available sources of energy fats as adipose tissue that can synthesize estrogens and can contribute to the circulation pool of estrogens. This leads to weight gain and it occurs several years prior to menopause. Fluctuating estrogen levels that occur during reproductive cycle events, particularly during the menopausal transition, is a time characterized by drastic fluctuations in estrogen levels and increases in new onset and recurrent depression. The decline in estrogen also affects the libido in woman, whereby treatment or efforts to increase estrogen and testosterone levels are employed to improve sexual desire and function.

Depletion in estrogen and an upregulation of FSH has been associated with occurrences of infertility amongst women and is prevalent as women age or suffer from chronic stress.

Hormonal imbalance can cause menopause. There are few treatment options available to manage hormonal imbalance, such as hormonal treatment therapy, as well as and herbal and homeopathic medications.

Clinically, menopause is defined as the state of an absence of menstrual periods for 12 months. The menopausal transition starts with varying menstrual cycle length and ends with the final menstrual period, where cessation of normal ovulation cycle takes place. A decrease in estradiol ($E_2$) production accompanies menopause, as the ovaries cease manufacture of $E_2$. The decrease in $E_2$ production results in a shift in hormone balance in the body, which often gives rise to a variety of symptoms associated with menopause. Since estrogen protects the bone, a woman can develop osteoporosis (thinning of bone) later in life when her ovaries do not produce adequate estrogen.

Peri-menopause, which is also known as pre-menopause, refers to the period prior to menopause during which normal ovulation cycles gradually give way to cessation of menses. Peri-menopause is often used to refer to the menopausal transitional period. It is not officially a medical term, but is sometimes used to explain certain aspects of the menopause transition in lay terms.

Post-menopause is a term used to refer to the time after menopause has occurred. For example, doctors may speak of a condition that occurs in "postmenopausal women." This refers to women who have already reached menopause.

The experience of women during menopause can differ from one to another. Some women may experience few or no symptoms of menopause, while others experience multiple physical and psychological symptoms. The extent and severity of symptoms varies significantly among women. The symptoms may come and go over an extended period for some women. This, too, is highly individual.

The symptoms that women experience are primarily related to a lowered production of the female sex hormones estrogen and progesterone. Symptoms vary widely because of the many effects that these hormones have on the female body. Estrogen regulates the menstrual cycle and affects the reproductive system, urinary tract, heart, blood vessels, bones, breasts, skin, hair, mucous membranes, pelvic muscles and brain.

The symptoms include physical symptoms such as hot flashes and sweating secondary to vasomotor instability. Additionally, psychological and emotional symptoms may accompany onset of climacteric, such as fatigue, irritability, mood swing, insomnia, inability to concentrate, depression, memory loss, headache, anxiety nervousness reduced fertility and sexual desire. Additional symptoms can include intermittent dizziness, paraesthesia, palpitations and tachycardia as well as nausea, constipation, diarrhoea, arthralgia, myalgia, cold hands and feet, breast tenderness, and weight gain. In addition, changes to the genitals, urinary incontinence, vaginal dryness, loss of pelvic muscle tone, increased risk of cardiovascular disease due to unfavourable change in cholesterol level and osteoporosis due to loss of bone increase with onset of menopause.

For decades hormone replacement therapy with estrogens has been the standard treatment for hot flashes, but many women have abandoned hormone therapy (HT) due to concerns about potential adverse effects, including breast cancer, heart disease, stroke and dementia as reported in recent studies, particularly the Women's Health Initiative (WHI). The observation that the selective estrogen receptor modulators ("SERMs") raloxifene and tamoxifen prevent estrogen receptor (ER) positive breast cancer provides additional evidence that estrogens promote breast cancer.

Estrogen deficiency following menopause results in skin changes and acceleration of skin aging by significantly modulating skin physiology, targeting keratinocytes, fibroblasts, melanocytes, hair follicles and sebaceous glands, and improving angiogenesis, wound healing and immune responses. Estrogen insufficiency decreases defence against oxidative stress; skin becomes thinner with less collagen, decreased elasticity, increased wrinkling, increased dryness and reduced vascularity. Its protective function becomes compromised and aging is associated with impaired wound healing, hair loss, pigmentary changes and skin cancer.

In many cases skin aging can be significantly delayed by the administration of estrogen. An application or upregulation of estrogens can alleviate the changes due to aging. The relevance of estrogen replacement, selective estrogen receptor modulators (SERMs) and phytoestrogens as therapies for diminishing skin aging is possible.

Botanical dietary supplements are used by many patients to relieve their menopausal symptoms. These include supplements used in Traditional Chinese Medicine (TCM), as well as phytoestrogens present in soybeans or herbal therapies as an alternative to estrogen, hoping to alleviate hot flashes without increasing their risk of developing breast cancer.

With the findings of the Woman's Health Initiative on risks of hormone therapy (HT) outweigh the benefits, a need for safer medicaments to alleviate symptoms and/or conditions associated with hormonal imbalance, including menopause has emerged.

*Eurycoma longifolia*, also known in Malaysia as Tongkat Ali, is a tropical herbal flowering plant in the family Simaroubacae found in several parts of South East Asia, primarily in Malaysia and Indonesia, and, to a lesser extent in Vietnam, Thailand and Laos. Locally it is also known as Penawar Bias, Muntah Bumi, Bedara Pahit, Lempedu Pahit, Penawar Pahit, Tongkat Baginda and Pasak Bumi Akar Jankat Semang, It is referred to as Bidara Laut in Indonesia, cay ba benh in Vietnamese and tho nan in Laotian.

Extracts or decoctions of *Eurycoma longifolia* are generally believed to be useful in the treatment of a wide variety of disorders and syndromes, such as malaria, cancer, anxiety, fatigue, migraine headaches, arthritis, diabetes, infections, fever, ulcers, male infertility and male sexual dysfunction. Due to the medicinal effects of this plant, extracts of *Eurycoma longifolia* have high commercial value in both the local and international markets.

Several effects of Tongkat Ali extract have been disclosed in the prior art, which include improving male sexual dysfunction, promoting the growth of sperm, improving sperm quality and other aspects of the treatment of infertility, increasing testosterone level in blood, promoting weight loss and treating obesity and its related disease.

European patent no. EP1952816 discloses a combination of herbal extracts to treat male sexual dysfunction. More specifically, this prior art discloses a combination of five different herbal extracts including Ginseng extract, Tongkat Ali extract, Epimedium extract, Gotu Kola extract and flower pollen extract to restore male erectile function. The composition has a promoting effect on penile erectility, so that it can be effectively used for the improvement of erectile dysfunction.

Chinese patent application publication number CN104666373 A discloses the use of *Eurycoma longifolia* Jack in preparation of drugs or health products for prevention and/or treatment on high blood sugar diseases. The *Eurycoma longifolia* Jack comprises quassia *Eurycoma longifolia* Jack or its decoction pieces or extract product. This disclosure provides an assistant hypoglycemic or hypoglycemic composition. The composition contains a *Eurycoma longifolia* Jack medical material or its decoction pieces or extract product. The *Eurycoma longifolia* Jack medical material or its decoction pieces or extract product or preparation, can be used for preventing or treating high blood sugar diseases such as diabetes, can produce good treatment effects in short time, can be used as a health food and has high safety.

Malaysia patent number MY-142166-A discloses the new use of bioactive compound derived from the *Eurycoma longifolia* jack for the treatment of obesity and obesity-related diseases. The bioactive compound comprises quassinoid, 13(21)-epoxyeurycomanone. This bioactive compound possesses activity of down-regulating the expression of specific protein that is over-expressed on blood vessel cells that serve only white fat tissue but absent on blood vessel cells of other tissues or organs. Therefore, the bioactive compound has the effects on inhibition or reduction of the formation of blood vessels in white fat tissue and eventually reverses the obesity and eventually obesity-related diseases.

Malaysia patent number MY-146000-A discloses a composition including a polar organic extract of *Eurycoma longifolia* and a fraction derived from the polar organic extract, said composition comprising of quassinoids, coumarins, their glycosides, analogues and derivatives, which exhibits bioactivity of increasing spermatozoa production and spermatozoa quality in terms of morphology and motility, as well as increasing testosterone synthesis and release from cells of males. The extraction method of *E. longifolia* plant to produce the polar organic extract, and the subsequent purification to produce the fraction of polar organic extract containing the quassinoids, coumarins, their glycosides, analogues and derivatives, and uses for manufacturing a preparation for infertility treatment are also provided. The fraction of polar organic extract containing the quassinoids, coumarins, their glycosides, analogues and derivatives is formulated for medical applications via several routes of administration.

Malaysia patent application number PI 20052294 discloses anti-cancer bioactive compounds of *Eurycoma longifolia* Jack that provides new uses and products for treatment of diseases and disease conditions. More particularly, this disclosure relates to the new uses of bioactive constituents' derived front the said herb for the treatments of cancers. Additionally, the invention relates the methods and processes of applying the said bioactive constituents into the said treatments. The said bioactive constituents comprise quassinoids and alkaloid wherein said quassinoids are eurycomanone and epoxveurvconianone, and said alkaloid is 9-niethoxycanthine-6-one, including all their respective analogues and derivatives of the said bioactive constituents. These bioactive constituents are used to irreversibly inhibit cancer cells growth and reduce the clonogenic capacities of the cancer cells at non-cytotoxic concentrations. Further, the bioactive constituents enhance the tumor suppressor activities, suppress the expression of cancer markers, suppress the expression of cancer-related genes, and modify the expression of genes associated with the controls of cell growth and functions.

Malaysia patent application number PI 2013001170 discloses *Eurycoma longifolia* stem, bark and/or root extract for use as adaptogen. In particular, for use in reducing and/or suppressing fatigue in a subject. More in particular, the extract may be used for improving physical and/or mental performance, for example physical endurance performance, like improving swimming performance.

Malaysia patent number MY-134867-A discloses new use and products for treatment of sexual dysfunction and male infertility. The products include bioactive components of extracts from roots of the plant *Eurycoma longifolia* mixed in preparations for topical application and administration.

Given the wide variety of therapeutic benefits of *Eurycoma longifolia* extracts, it is advantageous to provide an extract of this therapeutically valuable herbal medicine, used either alone or in combination for alleviating symptoms and/or conditions associated with hormonal imbalance in females, which includes menopause and its related symptoms.

SUMMARY OF THE INVENTION

As mentioned in the preceding paragraphs, the changes in level of estrogen, progesterone, follicle stimulating hormone (FSH) and luteinizing hormone (LH) in women results in a shift in hormone balance in the body, which often gives rise to a variety of symptoms and/or conditions associated with hormonal imbalance, which includes menopause and its related symptoms.

The symptoms and/or conditions associated with hormonal imbalance in females, which includes menopause and its related symptoms may have effect on the reproductive system, particularly the fertility rate, urinary tract, heart, blood vessels, bones, breasts, skin, hair, mucous membranes, pelvic muscles and brain.

Also in particular, the symptoms and/or conditions associated with hormonal imbalance in females, which includes menopause and its related symptoms can be characterized by the following hormonal changes:
 a decrease in serum estrogen level,
 a decrease in serum progesterone level,
 an increase in serum follicle stimulating hormone (FSH) level, and
 an increase in serum luteinizing hormone (LH) level.

To solve the problems of hormonal changes that results in a shift in a female's hormone balance in the body, the present invention provides a safe and effective treatment or alleviation of symptoms and/or conditions associated with hormonal imbalance, including menopause and its related symptoms, characterized by inducing changes in the level of estrogen, progesterone, follicle stimulating hormone (FSH) and luteinizing hormone (LH).

Simultaneously, the present invention provides a new kind of medicinal value or health care function of *Eurycoma longifolia* or traditionally known as Tongkat Ali.

It is therefore an object of the present invention to provide surprising and novel effects of *Eurycoma longifolia* extract for treating or alleviating symptoms and/or conditions associated with hormonal imbalance in females, including menopause and its related symptoms, characterized by inducing changes in the level of estrogen, progesterone, follicle stimulating hormone (FSH) and luteinizing hormone (LH).

In an embodiment of the present invention, the effect of the *Eurycoma longifolia* extract in respect of alleviating or treating symptoms and/or conditions associated to hormonal imbalance in females, including menopause and its related symptoms, is characterized by normalizing the hormonal content of estrogen, progesterone, follicle stimulating hormone (FSH) and luteinizing hormone (LH) in the blood, specifically by:
 increasing serum estrogen level by 0.3% to 16.0%,
 increasing serum progesterone level by 3.0% to 37.0%,
 decreasing serum follicle stimulating hormone (FSH) level by 7% to 26.0%,
 decreasing serum luteinizing hormone (LH) by 2.0% to 14.0%.

In particular, the present invention discloses the use of *Eurycoma longifolia* extract in the manufacture of a medicament to treat or alleviate symptoms and/or conditions associated with hormonal imbalance in females, including menopause and its related symptoms, which is characterized by normalizing the hormonal content of estrogen, progesterone, follicle stimulating hormone (FSH) and luteinizing hormone (LH).

In an embodiment, the effect of normalizing the hormonal content of estrogen, progesterone, follicle stimulating hormone (FSH) and luteinizing hormone (LH) is specifically characterized by:
 increasing serum estrogen level by 0.3% to 16.0%,
 increasing serum progesterone level by 3.0% to 37.0%,
 decreasing serum follicle stimulating hormone (FSH) level by 7% to 26.0%,
 decreasing serum luteinizing hormone (LH) level by 2.0% to 14.0%.

It is another object of the present invention to exploit the alleviation or treatment property of *Eurycoma longifolia* in respect of symptoms and/or conditions associated with hormonal imbalance in females, including menopause and its related symptoms, and to develop a pharmaceutical composition using this plant extract composition as an immediate alternative and evidence-based product to treat symptoms and/or conditions associated to hormonal imbalance in females, which includes menopause and its related symptoms.

Accordingly, a first aspect of the present invention provides the use of a composition comprising a therapeutically effective amount of *Eurycoma longifolia* extract in the manufacture of a medicament for alleviation or treatment of symptoms and/or conditions associated to hormonal imbalance in females, which includes menopause and its related symptoms.

Preferably, the composition comprises an aqueous extract of *Eurycoma longifolia*.

Preferably, the therapeutically effective amount of the extract ranges from 10 mg to 1000 mg.

More preferably, the therapeutically effective amount of the extract ranges from 50 mg to 500 mg.

According to the first aspect of the present invention, the medicament or composition for use in the manufacture of a medicament for alleviation or treatment of symptoms and/or conditions associated to hormonal imbalance in females, including menopause and its related symptoms, is characterized by inducing a change in the hormonal content of estrogen, progesterone, follicle stimulating hormone (FSH) and luteinizing hormone (LH).

In an embodiment, the effect of the medicament or composition comprising *Eurycoma longifolia* extract in respect of alleviating or treating symptoms and/or conditions associated to hormonal imbalance in females, including menopause and its related symptoms, is characterized by normalizing the hormonal content of estrogen, progesterone, follicle stimulating hormone (FSH) and luteinizing hormone (LH) in the blood, specifically by:

increasing serum estrogen level by 0.3% to 16.0%,
increasing serum progesterone level by 3.0% to 37.0%,
decreasing serum follicle stimulating hormone (FSH) level by 7% to 26.0%,
decreasing serum luteinizing hormone (LH) level by 2.0% to 14.0%.

In a second aspect of the present invention, there is provided the use of a pharmaceutical composition comprising a therapeutically effective amount of *Eurycoma longifolia* extract in the alleviation or treatment of symptoms and/or conditions associated to hormonal imbalance in females, including menopause and its related symptoms, wherein the alleviation or treatment of the symptoms and/or conditions is characterized by inducing a change in the hormonal content of estrogen, progesterone, follicle stimulating hormone (FSH) and luteinizing hormone (LH) in the blood.

According to a third aspect of the present invention, there is provided a method of alleviation or treatment of symptoms and/or conditions associated to hormonal imbalance in females, including menopause and its related symptoms, the method comprising the step of administering to a subject in need thereof a composition having a therapeutically effective amount of an extract derived from *Eurycoma longifolia*.

A further aspect of the present invention provides a method of treating or alleviating symptoms and/or conditions associated to hormonal imbalance, including menopause and its related symptoms, the method comprising the step of administering to a subject in need thereof a composition having a therapeutically effective amount of an extract derived from *Eurycoma longifolia*.

In a preferred embodiment, the subject in need is a mammal, The mammal may be a female human or a female animal.

According to another preferred embodiment of the present invention, the therapeutically effective amount of the extract is in a range of 10 mg to 1000 mg. More preferably, the therapeutically effective amount is in a range of 50 mg to 500 mg.

According to yet another preferred embodiment, the symptoms and/or conditions associated to hormonal imbalance, which includes menopause and its related symptoms, include lowered production of the female sex hormones estrogen and progesterone. Symptoms vary widely because of the many effects that these hormones have on the female body. Estrogen regulates the menstrual cycle and affects the reproductive system, particularly the fertility rate, urinary tract, heart, blood vessels, bones, breasts, skin, hair, mucous membranes, pelvic muscles and brain.

The symptoms include, but not limited physical symptoms such as hot flashes and sweating secondary to vasomotor instability. Additionally, psychological and emotional symptoms may accompany onset of climacteric, such as fatigue, irritability, insomnia, inability to concentrate, depression, memory loss, headache, anxiety and nervousness. Additional symptoms can include intermittent dizziness, paresthesia, palpitations and tachycardia as well as nausea, constipation, diarrhea, arthralgia, myalgia, cold hands and feet and weight gain. In addition, changes to the genitals, urinary incontinence, vaginal dryness, loss of pelvic muscle tone, increased risk of cardiovascular disease and osteoporosis increase with onset of menopause.

Still another preferred embodiment of the present invention discloses that the extract is an aqueous extract derived from *Eurycoma longifolia*. The extract may contain the major bioactive compound from *Eurycoma longifolia*.

One skilled in the art will readily appreciate that the present invention is well adapted to perform the objects and obtain the ends and advantages mentioned, as well as those inherent therein. The embodiments described herein are not intended as limitations on the scope of the invention.

DETAILED DESCRIPTION OF THE INVENTION

The treatment or ameliorative effect against symptoms and/or conditions associated to hormonal imbalance in females, including menopause and its related symptoms, according to the present invention, is provided by a new kind of medicinal value or health care function of *Eurycoma longifolia* or traditionally known as Tongkat Ali.

Accordingly, one aspect of the present invention provides the use of a composition comprising a therapeutically effective amount of *Eurycoma longifolia* extract in the manufacture of a medicament for alleviation or treatment of symptoms and/or conditions associated to hormonal imbalance in females, including menopause and its related symptoms.

Preferably, the composition comprises an aqueous extract of *Eurycoma longifolia*.

Preferably, the therapeutically effective amount of the extract ranges from 10 mg to 1000 mg.

More preferably, the therapeutically effective amount of the extract ranges from 50 mg to 500 mg.

According to the first aspect of the present invention, the medicament or composition for use in the manufacture of a medicament for alleviation or treatment of symptoms associated to hormonal imbalance in females, including menopause and its related symptoms, is characterized by inducing a change in the hormonal content of estrogen, progesterone, follicle stimulating hormone (FSH) and luteinizing hormone (LH) in the blood.

In an embodiment, the effect of the medicament or composition comprising *Eurycoma longifolia* aqueous extract in respect of alleviating or treating symptoms and/or conditions associated to hormonal imbalance in females, including menopause and its related symptoms, is characterized by normalizing the hormonal content of estrogen, progesterone, follicle stimulating hormone (FSH) and luteinizing hormone (LH) in the blood, specifically by:

increasing serum estrogen level by 0.3% to 16.0%,
increasing serum progesterone level by 3.0% to 37.0%,
decreasing serum follicle stimulating hormone (FSH) level by 7% to 26.0%,
decreasing serum luteinizing hormone (LH) level by 2.0% to 14.0%.

According to a second aspect of the present invention, there is provided the use of a pharmaceutical composition comprising a therapeutically effective amount of *Eurycoma longifolia* extract in the alleviation or treatment of symptoms and/or conditions associated to hormonal imbalance in females, including menopause and its related symptoms, wherein the alleviation or treatment of symptoms and/or conditions associated to hormonal imbalance, including menopause and its related symptoms is characterized by inducing changes and normalizing the hormonal content of estrogen, progesterone, follicle stimulating hormone (FSH) and luteinizing hormone (LH) in the blood.

According to a third aspect of the present invention, there is provided a method of alleviation or treatment of symptoms and/or conditions associated to hormonal imbalance, including menopause and its related symptoms, the method comprising the step of administering to a subject in need thereof a composition having a therapeutically effective amount of an extract derived from *Eurycoma longifolia*.

A further aspect of the present invention provides a method of treating or alleviating symptoms and/or conditions associated to hormonal imbalance, including menopause and its related symptoms, the method comprising the step of administering to a subject in need thereof a composition having a therapeutically effective amount of an extract derived from *Eurycoma longifolia*.

In a preferred embodiment, the subject in need is a mammal, The mammal may be a female human or a female animal.

According to another preferred embodiment of the present invention, the therapeutically effective amount of the extract is in a range of 10 mg to 1000 mg. More preferably, the therapeutically effective amount is in a range of 50 mg to 500 mg.

According to yet another preferred embodiment, the symptoms and/or conditions associated to hormonal imbalance, including menopause and its related symptoms, include lowered production of the female sex hormones estrogen and progesterone. Symptoms vary widely because of the many effects that these hormones have on the female body. Estrogen regulates the menstrual cycle and affects the reproductive system, urinary tract, heart, blood vessels, bones, breasts, skin, hair, mucous membranes, pelvic muscles and brain.

The symptoms include, but not limited to physical symptoms such as hot flashes and sweating secondary to vasomotor instability. Additionally, psychological and emotional symptoms may accompany onset of climacteric, such as fatigue, irritability, insomnia, reduced fertility, inability to concentrate, depression, memory loss, headache, anxiety and nervousness. Additional symptoms can include intermittent dizziness, paraesthesia, palpitations and tachycardia as well as nausea, constipation, diarrhea, arthralgia, myalgia, cold hands and feet and weight gain. In addition, changes to the genitals, urinary incontinence, vaginal dryness, loss of pelvic muscle tone, increased risk of cardiovascular disease and osteoporosis increase with onset of menopause.

The extract of *Eurycoma longifolia* as described herein contains the desired active ingredients from the *Eurycoma longifolia* plant, which may be further subjected to separation and characterization.

The extract is obtained by way of extraction procedures that are known in the art, which include the basic steps of pre-washing, drying or freeze-drying of the plant materials (e.g. root), grinding the plant materials to obtain a homogeneous sample and often improving the kinetics of analytic extraction and also increasing the contact of sample surface with an aqueous system. Proper actions must be taken to assure that potential active ingredients/constituents are not lost, distorted or destroyed during the preparation of the extract from the *Eurycoma longifolia* plant sample.

The extract thus obtained may be ready for use as a medicinal agent in its original dry extract form, the form of tinctures and fluid extracts, it may be further processed to be incorporated in any dosage form such as tablets or capsules, or it may be fractionated to isolate individual chemical entities. Thus, standardization of extraction procedures contributes significantly to the final quality of the herbal drug.

In a preferred embodiment, the extract of *Eurycoma longifolia* is an aqueous extract. The aqueous extract can be obtained by any known extraction method, for example boiling air-dried powdered plant part (e.g. roots) in water for approximately 10 minutes and then subjecting to cooling to room temperature. The aqueous extract is then filtered to remove particulate matter. The final volume of each filtrate can then be completed to 100 ml with distilled water with 0.2% Tween 80 to account for the evaporated water during boiling.

The extract of *Eurycoma longifolia* that is capable of treating or alleviating symptoms and/or conditions associated to hormonal imbalance, including menopause and its related symptoms comprises the following active ingredients:

TABLE 1

| Ingredient | Amount (w/w) | Preferred amount (w/w) |
|---|---|---|
| Eurycomanone | 0.3 to 3.5% | 0.8 to 2.5% |
| Total protein | more than 10% | more than 22% |
| Total polysaccharide | more than 20% | more than 30% |
| Glycosaponin | more than 30% | more than 40% |

The present invention further provides a method for treating or alleviating symptoms and/or conditions associated to hormonal imbalance, including menopause and its related symptoms, in an individual female.

One embodiment of this method includes administering to the individual female an effective amount of an extract of *Eurycoma longifolia*.

The effective amount to treat or alleviate the symptoms and/or conditions associated to hormonal imbalance, including menopause and its related symptoms, will depend on the severity of the condition being treated; individual patient parameters including age, physical condition, size and weight; concurrent treatment and drug interaction; frequency of treatment; and the mode of administration.

Preferably, the effective amount of the extract is 10 mg to 1000 mg. More preferably, the effective amount is 50 mg to 500 mg.

To assess the properties of the *Eurycoma longifolia* extract, a variety of experiments were performed using formulations of the extract. Details of the experiments are provided in the examples below.

In an embodiment, in addition to *Eurycoma longifolia* derived-compositions, e.g. extracts of *Eurycoma longifolia*, the preparation of the present invention includes a pharmaceutically or nutraceutically acceptable carrier for oral administration.

In order to facilitate oral administration, *Eurycoma longifolia* derived compositions may be mixed with any of a variety of pharmaceutically acceptable carriers for oral administration. By the term "pharmaceutically or nutraceutically acceptable carrier for oral administration" is meant a composition which is non-toxic, is not irritating to the human gastrointestinal system, and which can be mixed with *Eurycoma longifolia* derived compositions to form a solution, syrup, emulsion, gel, powdered mix or solid. Preparations for intravenous, intramuscular, subcutaneous or, in general, parenteral administration may also be produced by methods known in the art.

The pharmaceutically or nutraceutically acceptable carriers for oral administration may include, but not limited to sugars such as lactose, glucose and sucrose; starches such as corn starch and potato starch; cellulose and its derivatives, such as sodium carboxymethycellulose, ethylcellulose, and cellulose acetate; powdered tragacanth; malt; gelatin; talc; stearic acid; magnesium stearate; calcium sulfate; vegetable oils such as corn oil, cotton seed oil, and olive oil; polyols such as propylene glycol, glycerine, sorbitol, mannitol, and polyethylene glycol; phosphate buffer solutions; cocoa butter; emulsifiers; as well as other non-toxic compatible substances used in pharmaceutical formulations. Wetting agents and lubricants such as magnesium stearate, as well as coloring agents, flavouring agents, excipients, tableting agents, stabilizers, antioxidants, and preservatives, can also be present. Other compatible pharmaceutical additives and actives may be included in the pharmaceutically acceptable carrier for use in the compositions of the present invention.

The preparations for oral administration may be in the form of tablets, caplets, soft and hard gelatine capsules, pills including delayed or slow or modified release formulations, dispersible powders or granules, lozenges, sachets, cachets, suspensions, emulsions, solutions, syrups, aerosols, and the like.

One embodiment where use of a composition for treating or alleviating an individual from symptoms and/or conditions associated to hormonal imbalance, including menopause and its related symptoms, is the administration to a subject an extract derived from *Eurycoma longifolia*.

As used herein the subject is a human, non-human primate, cattle, horse, pig, sheep, goat, dog, cat, fish, prawn, chicken, rodent and many more. In all embodiments human female subjects are preferred.

The *Eurycoma longifolia*-derived composition can be formulated and administered in effective amounts, alone or in a cocktail with other compounds. An effective amount is one sufficient to treat or alleviate symptoms and/or conditions associated to hormonal imbalance in females, including menopause and its related symptoms.

Effective amounts will depend, of course, on the severity of the condition being treated; individual patient parameters including age, physical condition, size and weight; concurrent treatment; frequency of treatment; and the mode of administration. These factors are well known to those of ordinary skill in the art and can be addressed with no more than routine experimentation. It is preferred generally that a maximum dose be used, that is the highest safe dose according to sound medical judgement.

Generally, daily doses of active compounds will be from about 10 milligrams per day to 1000 milligrams per day. It is expected that oral doses in the range of 50 to 500 milligrams, in one or several administrations per day, will yield the desired results. In the event that the response in a subject is insufficient at such doses, even higher doses (or effective higher doses by a different, more localized delivery route) may be employed to the extent that patient tolerance permits. Dose ranges can be adjusted as necessary for the treatment of individual patients and according to the specific condition treated. Multiple doses per day are contemplated to achieve appropriate systemic levels of compounds.

The methods of the present invention may be practiced using any mode of administration that is medically acceptable, which produces effective levels of the active compounds without causing clinically unacceptable adverse effects. Such modes of administration include oral, rectal, topical, nasal, transdermal or parenteral routes. The term "parenteral" includes subcutaneous, intravenous, intramuscular, or infusion. Intravenous and intramuscular routes are not particularly suited for long term therapy and prophylaxis.

The compositions may conveniently be presented in unit dosage form and may be prepared by any of the methods well known in the art. In general, the compositions are prepared by uniformly and intimately bringing the active compounds into association with a liquid carrier, a finely divided solid carrier, or both, and then, if necessary, shaping the product.

Compositions suitable for oral administration may be presented as discrete units such as capsules, cachets, tablets, soft gels or lozenges, each containing a predetermined amount of the active compound. Other compositions include suspensions in aqueous liquors or non-aqueous liquids such as syrup or an emulsion.

The present invention will now be described in further detail by way of non-limiting examples.

EXAMPLE 1

Preparation of *Eurycoma longifolia* Aqueous Extract

Aqueous extract of *Eurycoma longifolia* was prepared, characterised by comprising 0.8-2.5% eurycomanone, >22% total protein, >30% total polysaccharide and >40% glycosaponin, which was used to assess the bioactivity of *Eurycoma longifolia*.

Method 1000 kg *Eurycoma longifolia* ("Tongkat Ali") wood chips was dried and grinded before being placed in a percolation tank. 5000 L of purified water was filled in the tank, which was then heated up to 105° C.±20° C. The heated water was allowed to circulate and percolated through the tank for approximately 4-7 hours. All the miscera was discharged through filters for concentration. The miscera was concentrated by thin layer, heat and vacuum. The concentration process was continued until a concentrate of solid content of 10-40% was obtained. The concentrate was then subjected to drying and milled into fine powders. The extract was then utilised in bioactivity experiments as described in the following example.

EXAMPLE 2

Assessment on the Bioactivity of *Eurycoma longifolia* Extract—Alleviation of Symptoms Associated to Hormonal Imbalance in Females and Menopause Symptoms The test item, i.e. aqueous extract of *Eurycoma longifolia*, was studied for its capabilities or effect in relation to the alleviation or treatment of menopause symptoms and hormonal activity against ovariectomized rat model in vivo.

48 female Sprague dawley rats were ovariectomized or sham operated. Both sham and ovariectomized rats (n=8) received the vehicle. The remaining 3 group ovariectomized rats were orally administered with *Eurycoma longifolia* aqueous extract 100 mg/kg, 300 mg/kg and 500 mg/kg b.w. The treatment continued for 8 weeks. Group 6 ovariectomized rats received testosterone undecanoate (10 mg/kg b.w) through the route of intramuscular injection once in every 4 weeks for 8 weeks. At week 8 of the last dose, sexual behaviors were recorded. Blood was collected for biochemical analysis. Calcium, phosphate, bone alkaline phosphatase (ALP), osteocalcin and hormone profile estimation was done. The result of present study revealed that treatment with *Eurycoma longifolia* aqueous extract can become a potential choice of alleviating or treating hormonal imbalance in females and menopausal symptoms.

Objective

The broad objective of this study is to evaluate the potential of the *Eurycoma longifolia* extract to replace hormone therapy for treating or alleviating symptoms and/or conditions associated to hormonal imbalance in females, including menopause and its related symptoms, using ovariectomized rat model in vivo.

Specifically, the objectives of the present study are outlined below:

to determine the effects of *Eurycoma longifolia* extract on the reproductive hormones, i.e. follicle stimulating hormone (FSH), luteinizing hormone (LH), estrogen, progesterone and testosterone, of experimental ovariectomized rats.

Test Item

The test item used in this methodology is an aqueous extract of *Eurycoma longifolia* that was obtained by way of the extraction method described in Example 1.

The physical appearance of the test item is light brown powder and is preferably stored in an airtight closed container at room temperature in dry place with low relative humidity.

Since the test item is completely soluble in water, water was used as vehicle to prepare suspension of the extract test item.

Test System
Animal species: Rats
Strain: Sprague Dawley
Justification for Selection of Species: Recommended and Justified by sponsor
Sex: Female
Age: 10-12 weeks (Mohamed et al, 2016)
Source of supply: In house breed
No. of groups: 6
  Group 1: Sham operated group (surgically opened but no ovariectomy)
  Group 2: Ovariectomy group (Negative control)
  Group 3: Ovariectomy+Low dose extract
  Group 4: Ovariectomy+Middle dose extract
  Group 5: Ovariectomy+High dose extract
  Group 6: Ovariectomy+Testosterone undecanoate (Positive control)
No. of Animals/Group: 8 females/group
Age at Treatment: 12 weeks
Body Weight Range at Receipt: 120-250 gms
Animal Identification: Each animal will be marked by picric acid and numbering will be given individually to each animal.
Acclimatization: The rats were acclimatized for 1 week before treatment.
Husbandary
  a. Environmental Conditions: Animals will be housed under temperature 22±3° C., relative humidity 30-70%, 12 hour light and 12 hour dark cycle.
  b. Housing: The animals were housed in a group of 8 in a standard polypropylene cage with stainless steel top grill having facilities for pelleted food and drinking water in bottle; paddy husk was used as bedding material and changed at least twice a week.
  c. Feed ad libitum: Normal chow diet will be provided to all the animals throughout the experiment.
  d. Water ad libitum: Aqua guard on line water will be provided ad libitum. Animals should have continuous access to fresh, potable, uncontaminated drinking water.

Acclimatization

Healthy and young adult animals were acclimatized for a period of seven days to laboratory conditions prior to treatment and were observed for clinical signs once daily. Veterinary examination of all the animals was performed on the day of receipt and 7th day of acclimatization.

Grouping

Grouping was done by the method of body weight stratification and randomization. After acclimatization period healthy animals was weighed and randomly allotted to 6 groups (8 animals per group) as mentioned in the study design.

Study Design

The selected animals were assigned to different groups as shown below: in Table 2.

TABLE 2

| Groups | Group Description | Treatment Description | Dose Volume (ml/kg) | Animals/Group |
|---|---|---|---|---|
| Group 1 | Sham operated group | Surgery was performed but ovary was not be dissected. | 10 | 8 |
| Group 2 | Ovariectomy (Ovx) group (Negative control) | Surgery was performed and ovaries were removed (Ovariectomized). | 10 | 8 |
| Group 3 | Ovx + Low dose extract - daily | Ovariectomized animals were treated with herbal extract at low dose (100 mg/kg). | 10 | 8 |
| Group 4 | Ovx + Middle dose extract - daily | Ovariectomized animals were treated with herbal extract at middle dose (300 mg/kg). | 10 | 8 |
| Group 5 | Ovx + High dose extract - daily | Ovariectomized animals were treated with herbal extract at high dose (500 mg/kg). | 10 | 8 |

TABLE 2-continued

| Groups | Group Description | Treatment Description | Dose Volume (ml/kg) | Animals/ Group |
|---|---|---|---|---|
| Group 6 | Ovx + Testosterone undecanoate (Positive control) - Once in every 4 weeks | Ovariectomized animals were treated with Testosterone undecanoate (10 mg/kg) intra muscular injection. | 10 | 8 |

Preparation of Test Item

Formulation preparation was carried out by trituration method using mortar and pestle. The test substance formulation was prepared daily. A known amount of 100 mg, 300 mg and 500 mg of *Eurycoma longifolia* aqueous extract weighed separately and added to separate mortars. Slowly small quantity of Carboxy Methyl Cellulose sodium suspension was added to each mortar with stirring continuously by a pestle. Then, quantity sufficient volume was made using the vehicle (Carboxy Methyl Cellulose sodium suspension) and stirred 5 minutes for uniform suspension. Total 10 ml of vehicle was added to each formulation. This was continued every day for preparing formulation freshly. Quantity of formulation depends on animal body weight and it was 10 ml/kg body weight.

Dose Selection and Justification for Selection

The above prepared solutions were administered at a dose of 10 ml/kg. Actual dose volumes were based on the most recently recorded body weight.

Route of Administration and Justification for Selection

The present formulation is intended for oral use in clinical conditions. Particularly, the present formulation was given by oral gavage to group 3-5.

Administration of Test Item

The test item solution was administered through oral route at a dose volume of 10 mL/kg body weight daily for 8 weeks.

Procedure

After acclimatization of 1 week, animals were divided into six groups of 8 rats in each group. Ovariectomy was performed under aseptic conditions in all the animals of Group 2 to Group 6 under anesthesia. In Group 1 animals, surgery was performed using same procedure but ovaries were not dissected.

In Group 2, only ovariectomy was performed. Group 3, Group 4 and Group 5 received the *Eurycoma longifolia* aqueous extract daily at low dose (100 mg/kg), middle dose (300 mg/kg) and high dose (500 mg/kg) at respective concentrations orally for 8 weeks, whereas Group 6 received Testosterone undecanoate (10 mg/kg) intramuscular injection once in every 4 weeks for 8 weeks.

(i) Surgical Procedure

Anesthesia was induced by intraperitoneal injection of ketamine HCL (80 mg/kg) and the depth of anesthesia was checked by monitoring respiratory rate or simply testing the animal response to gentle pressure on the hind paws. After the onset of anesthesia, animal was placed under operating area. Clippers were used to clip the skin and shaved fur bilaterally to expose skin. The procedure was carried out by making two incisions to separately reach each ovary. Shaved skin was swab with 70% (v/v) ethanol. Anaesthetized animal was placed on the operating table with its back exposed and its tail towards the operator. A single dorsal incision (1 cm) was made penetrating the skin using small scissors. Incision was made in the lower back, directly below the bottom of the rib cage. Gently subcutaneous connective tissue was made free from the underlying muscle on each side using blunt forceps. Ovary was located under the thin muscle layer and a small incision (less than 1 cm) was made on each side to gain entry to the peritoneal cavity. The edge of the incision was holded securely with tooth forceps and the ovarian fat pad was retracted surrounding ovaries with blunt forceps to expose oviduct. Ovary was removed by gently severing the oviduct, using sterile, small scissors. Uterus was replaced and remaining part of the oviduct back into the abdominal cavity. Muscle layer was sutured and procedure was repeated for the other ovary. A suitable analgesic (meloxicam) was administered post operatively.

(ii) Observation

The following observations were made during the experiment.

Clinical Signs and Mortality

Each animal was observed for mortality, common signs, and signs of pain and distress at least once daily.

Body Weight

Body weight was recorded before surgery, weekly thereafter and at the end of the dosage schedule.

Feed Consumption

Feed intake was carried out daily during the study period. 30 gms feed was added daily to each animal in the morning time and leftover feed was recorded on next day from the same animal cage. Feed consumption was averaged, calculated and expressed as g/animal/day.

Necropsy

Animals were sacrificed using extended isoflurane anesthesia and further subjected to necropsy, isolated the uterus and uterus weight was recorded in all the group of animals.

Biochemical Estimations

At the end of eight weeks, all the animals were fasted overnight but free access to water, on the next day animals were anaesthetized by isoflurane anesthesia and 500 µl blood samples was withdrawn by retro orbital route and samples were then centrifuged for 10 min at 3000 rpm for the separation of serum. Separated serum was stored at −80° C. until to carry out biochemical analyses.

Calcium and Phosphates were analyzed by using fully Automated Clinical Chemistry Analyzer EM360, TransasiaBio-medicals Ltd. Calcium was analyzed by using ERBA calcium kit (Lot No: B071648) by the method of aresenazo III. Phosphate was analyzed by using ERBA Phosphate kit (Lot No: B071630) by ammonium molybdate method using biochemistry EM 360 analyzer. Bone type of alkaline phosphatase was assayed by using Elabsciences ELISA kit (Cat No.: E-EL-R1109). Osteocalcin was tested using Elabscinces ELISA kit (Cat No.: E-EL-R0243).

Follicle Stimulating Hormone was analyzed by using Roche Follicle Stimulating Hormone kit (Lot No: 033208), Luteinizing Hormone was analyzed by using Roche Luteinizing Hormone kit (Lot No: 030208). Estrogen was analyzed by using Roche Estradiol kit (Lot No: 127038), Progesterone was analyzed by using Roche progesterone kit (Lot No: 0278) and Testosterone was tested using Roche Testosterone kit (Lot No: 180003). All these reproductive hormone estimations were done by the method of C4SA (CLIA (Chemiluminescence immunoassay)) by using Siemens fully auto analyzer.

Statistical Analysis

All data including body weight, feed consumption, biochemical evaluation and organ weights were statistically analyzed using Graph-Pad Prism Software, version 5.01. All values were expressed as mean±SEM. The significant difference between the treatment and control group was estimated using one-way ANOVA with Tukey's post test. In any case the values were considered statistically significant at $P<0.05$.

EXAMPLE 3

Results and Conclusion

Menopausal is the time of life when menstrual cycle ceases and is caused by reduced secretion of the ovarian hormones and progesterone which is characterized by low bone mass and it leads to enhanced bone fragility. Many symptoms have been attributed menopause. Common symptoms such as mood changes sleep disturbances, urinary incontinence, cognitive changes and sexual dysfunction. Hormone deficiency especially estrogen is considered as the main determinant in post-menopausal women. Osteoporosis is caused by an imbalance in the normal bone remodeling process in which there is excessive osteoclast resorption and adequate new bone formation by osteoblast reduction.

Hormone replacement therapy has proven to be efficacious in preventing bone loss and reducing symptoms in post-menopausal women. Instead of hormone replacement therapy we are tested herbal extract to reduce menopausal symptoms in ovariectomized rats.

(i) Clinical Signs and Mortality

As shown in Table 3, all the treated animals were observed daily for signs of toxicity, common signs and behavioral changes. *Eurycoma longifolia* aqueous extract did not cause any adverse or toxic effects during the treatment period. Further, treated animals experienced no changes in general behavior.

TABLE 3

Summary of Clinical Signs of Toxicity and Mortality

| Groups | Group Description | No. of Animals | Clinical Signs of Toxicity | No. of Mortality/ No. of Animals Dosed |
|---|---|---|---|---|
| Group 1 | Sham control (10 ml/kg) | 8 | N | 0/8 |
| Group 2 | Negative control (10 ml/kg) | 8 | N | 0/8 |

TABLE 3-continued

Summary of Clinical Signs of Toxicity and Mortality

| Groups | Group Description | No. of Animals | Clinical Signs of Toxicity | No. of Mortality/ No. of Animals Dosed |
|---|---|---|---|---|
| Group 3 | Low dose (100 mg/kg) | 8 | N | 0/8 |
| Group 4 | Mid dose (300 mg/kg) | 8 | N | 0/8 |
| Group 5 | High dose (500 mg/kg) | 8 | N | 0/8 |
| Group 6 | Positive Control(10 ml/kg) | 8 | N | 0/8 |

(ii) Body Weight

Ovariectomy induces an increase in body weight, also in the present study the body weight of the animals increased after ovariectomy and the increase was slowly inhibited by the administration of the *Eurycoma longifolia* aqueous extract.

Table 4A and 4B represent the body weight of rats; basal body weight showed equal average weight in each group and it was increased drastically from basal to week 8 in ovariectomized groups. *Eurycoma longifolia* aqueous extract treated high dose (500 mg/kg b.w) group showed a decrease in body weight when compared to negative control group. In sham control group animals showed normal increase in body weight but it was normal pattern of body weight growth from basal to week 8 when compared to ovariectomized rats.

Body weight in sham control group showed 186.8±9.60 to 242.1±7.62 from basal to week 8.

Referring to Table 4A and 4B, the body weight did not increase drastically in herbal extract high dose treated group (252.5±8.31) when compared to negative control group (261.1±7.73). *Eurycoma longifolia* aqueous extract treated groups prevents increase in body weight and it was seen in dose dependent manner. Increase in body weight observed from basal to week 8 and it is expressed in percent. Group 1 showed 5.14% in week 1 and 29.60% in week 8. Group 2 was found to be 5.56% and 41.06% in week 1 and week 8 respectively. *Eurycoma longifolia* aqueous extract treated Group 3, Group 4 and Group 5 was found to be 5.72%, 5.61% and 4.95% in week 1 and 39.43%, 36.95% and 35.90% in week 8 respectively. Percent weight gain in Group 6 was 5.95% in week 1 and 40.16% in week 8. No significant changes were observed in percent of weight gain.

Regarding the role of estrogen in lipid metabolism, estrogen insufficiency is thought to be largely responsible for an increase in adiposity during menopause because post-menopausal women under hormone replacement therapy do not display characteristic pattern of abdominal weight gain usually associating with menopause. Hence, the *Eurycoma longifolia* aqueous extract is able to regulate the lipid metabolism.

TABLE 4A

Summary of Effect of Herbal Extract on Rats Body Weight

| Group | Basal | Week 1 | Week 2 | Week 3 | Week 4 | Week 5 | Week 6 | Week 7 | Week 8 |
|---|---|---|---|---|---|---|---|---|---|
| Group 1 Sham Control | 186.8 ± 9.60 | 196.4 ± 9.71 | 207.6 ± 9.07 | 214.9 ± 9.14 | 222.9 ± 9.80 | 227.4 ± 9.46 | 232.4 ± 9.02 | 237.9 ± 7.38 | 242.2 ± 7.62 |
| Group 2 Negative Control | 185.1 ± 5.45 | 195.4 ± 5.98 | 206.0 ± 5.67 | 219.5 ± 5.81 | 231.5 ± 5.75 | 240.4 ± 6.44 | 247.9 ± 6.83 | 255.3 ± 7.45 | 261.1 ± 7.73 |
| Group 3 Low Dose 100 mg/kg | 185.4 ± 5.32 | 196.0 ± 5.62 | 207.1 ± 5.68 | 217.0 ± 5.84 | 228.1 ± 5.82 | 236.1 ± 6.09 | 242.8 ± 6.36 | 251.9 ± 6.42 | 258.5 ± 6.82 |
| Group 4 Mid Dose 300 mg/kg | 185.4 ± 6.28 | 195.8 ± 5.77 | 206.9 ± 5.20 | 217.6 ± 5.11 | 227.4 ± 5.49 | 234.6 ± 5.94 | 241.0 ± 6.43 | 248.9 ± 6.76 | 253.9 ± 7.20 |
| Group 5 High Dose 500 mg/kg | 185.8 ± 6.23 | 195.0 ± 6.96 | 206.4 ± 6.84 | 217.3 ± 6.92 | 226.9 ± 7.20 | 233.9 ± 7.63 | 239.9 ± 7.99 | 247.3 ± 8.44 | 252.5 ± 8.31 |
| Group 6 Positive Control | 185.0 ± 3.35 | 196.0 ± 3.17 | 207.4 ± 2.99 | 217.8 ± 3.31 | 229.4 ± 3.24 | 238.6 ± 3.33 | 244.8 ± 3.53 | 252.9 ± 4.37 | 259.3 ± 4.85 |

TABLE 4B

Summary of Effect of Herbal Extract on Percentage (%) of Weight Gain in Rat Body Weight

| Group | Week 1 | Week 2 | Week 3 | Week 4 | Week 5 | Week 6 | Week 7 | Week 8 |
|---|---|---|---|---|---|---|---|---|
| Group 1 | 5.14 | 11.13 | 15.04 | 19.33 | 21.73 | 24.41 | 27.36 | 29.60 |
| Group 2 | 5.56 | 11.29 | 18.58 | 25.07 | 29.88 | 33.93 | 37.93 | 41.06 |
| Group 3 | 5.72 | 11.70 | 17.04 | 23.03 | 27.35 | 30.96 | 35.87 | 39.43 |
| Group 4 | 5.61 | 11.60 | 17.37 | 22.65 | 26.54 | 29.99 | 34.25 | 36.95 |
| Group 5 High | 4.95 | 11.09 | 16.95 | 22.12 | 25.89 | 29.12 | 33.10 | 35.90 |
| Group 6 | 5.95 | 12.11 | 17.73 | 24.00 | 28.97 | 32.32 | 36.70 | 40.16 |

(iii) Feed Consumption

As represented in Table 5, feed consumption or feed intake revealed no significant changes in average feed intake in all the groups from week 01 to week 08. Average feed consumption from week 01 to week 08 was found to be 15.0 to 20.2 grams.

TABLE 5

Summary of Effect of *Eurycoma longifolia* Aqueous Extract on Feed Intake in Rats

| Groups | Basal | Week 01 | Week 02 | Week 03 | Week 04 | Week 05 | Week 06 | Week 07 | Week 08 |
|---|---|---|---|---|---|---|---|---|---|
| Group 1 Sham control | 15.7 ± 0.4 | 18.6 ± 0.1 | 19.2 ± 0.0 | 19.2 ± 0.0 | 19.7 ± 0.0 | 20.1 ± 0.1 | 20.1 ± 0.1 | 20.2 ± 0.0 | 15.7 ± 0.4 |
| Group 2 Negative control | 15.2 ± 0.4 | 18.5 ± 0.1 | 19.2 ± 0.1 | 19.3 ± 0.1 | 19.8 ± 0.1 | 20.1 ± 0.1 | 20.1 ± 0.0 | 20.2 ± 0.1 | 15.2 ± 0.4 |
| Group 3 Low dose | 15.5 ± 0.3 | 18.5 ± 0.1 | 19.3 ± 0.1 | 19.3 ± 0.0 | 19.7 ± 0.0 | 20.1 ± 0.1 | 20.1 ± 0.0 | 20.2 ± 0.0 | 15.5 ± 0.3 |
| Group 4 Mid dose | 15.3 ± 0.4 | 18.8 ± 0.0 | 19.3 ± 0.1 | 19.3 ± 0.0 | 19.7 ± 0.0 | 20.0 ± 0.0 | 20.0 ± .0 | 20.1 ± 0.0 | 15.3 ± 0.4 |
| Group 5 High dose | 15.0 ± 0.3 | 18.3 ± 0.0 | 19.2 ± 0.0 | 19.2 ± 0.0 | 19.7 ± 0.0 | 20.1 ± 0.0 | 20.0 ± 0.1 | 20.2 ± 0.0 | 15.0 ± 0.3 |
| Group 6 Positive control | 15.4 ± 0.4 | 18.8 ± 0.0 | 19.3 ± 0.1 | 19.4 ± 0.0 | 19.9 ± 0.1 | 20.1 ± 0.0 | 20.1 ± 0.0 | 20.2 ± 0.0 | 15.4 ± 0.4 |

(iv) Biochemical Estimations

Table 6 represents the results of effects of *Eurycoma longifolia* aqueous extract on calcium, phosphate, bone type of alkaline phosphatase (ALP) and osteocalcin levels in treated animals.

Bone Alkaline Phosphatase

Still referring to Table 6, the bone alkaline phosphatase (ALP) level significantly decreased (P<0.001, 2.54±0.20) in negative control group when compared to sham control. The level of bone ALP significantly increased (P<0.05,

TABLE 6

| Groups | Calcium (mg/dl) | Phosphate (mg/dl) | Bone Alkaline phosphatase (ng/ml) | Osteocalcin (ng/ml) |
|---|---|---|---|---|
| Group 1 Sham control | 9.05 ± 0.20 | 3.71 ± 0.14 | 3.43 ± 0.11 | 7.13 ± 0.34 |
| Group 2 Negative control | 7.86 ± 0.12### | 2.83 ± 0.12### | 2.54 ± 0.20### | 7.86 ± 0.48 |
| Group 3 Low dose 100 mg/kg | 7.85 ± 0.12 | 2.83 ± 0.11 | 2.57 ± 0.04 | 7.89 ± 0.06 |
| Group 4 Mid dose 300 mg/kg | 7.98 ± 0.11 | 2.89 ± 0.08 | 2.70 ± 0.11 | 7.79 ± 0.21 |
| Group 5 High dose 500 mg/kg | 8.11 ± 0.11 | 3.01 ± 0.12 | 2.82 ± 0.10 | 7.52 ± 0.18 |
| Group 6 Positive control | 8.48 ± 0.16* | 3.29 ± 0.13* | 3.06 ± 0.12* | 7.26 ± 0.20 |

P < 0.05,
P < 0.01 and
P < 0.001 vs. Group 1;
*P < 0.05,
**P < 0.01 and
***P < 0.001 vs. Group 2.

Calcium

Referring to Table 6, there was significant decrease in serum calcium level in negative control group (P<0.001, 7.86±0.12) when compared to sham control and significant increase in calcium level in positive control group (P<0.05, 8.48±0.16) as compared to negative control. Increasing trend was seen in treatment group in dose dependent manner.

Phosphate

Referring to Table 6, serum phosphate level decreased significantly (P<0.001, 2.83±0.12) in negative control group as compared to sham control, Serum phosphate level increased significantly (P<0.05, 3.29±0.13) in positive control group as compared to negative control.

All the *Eurycoma longifolia* extract treated groups shows increased serum phosphate level when compared to negative control group. Increasing trend was seen in treatment group in dose dependent manner.

3.06±0.12) in positive control group as compared to negative control. Increasing trend was seen in treatment group in dose dependent manner.

Osteocalcin

In this study, the mean levels of serum osteocalcin were found also to be increased in ovariectomized rats when compared with the sham control. This increased level of serum osteocalcin in the ovariectomized rat group is attributed to the induced oestrogen deficiency. Elevated level of serum osteocalcin, is a marker of bone turnover. Decreased serum osteocalcin levels were observed in *Eurycoma longifolia* aqueous extract treated groups and positive control groups, but no significant changes were noticed in all the treated groups.

Table 7 represents the effects of *Eurycoma longifolia* aqueous extract on reproductive hormone levels in rat serum:

TABLE 7

| | Summary of Effect of Herbal Extract on Follicle Stimulating Hormone (FSH), Lutenizing Hormone (LH), Progesteron, Estrogen and Testosterone in Rats | | | | |
|---|---|---|---|---|---|
| Group | FSH (mIU/ml) | LH (mIU/ml) | Progesterone (ng/ml) | Estrogen (pg/ml) | Testosterone (ng/ml) |
| Group 1 Sham control | 2.26 ± 0.07 | 1.73 ± 0.05 | 5.78 ± 0.25 | 29.31 ± 0.60 | 4.48 ± 0.21 |
| Group 2 Negative control | 5.70 ± 0.33### | 4.69 ± 0.22### | 1.82 ± 0.09### | 9.49 ± 0.27### | 1.22 ± 0.06### |
| Group 3 Low dose 100 mg/kg | 5.29 ± 0.27 | 4.57 ± 0.18 | 1.88 ± 0.05 | 9.52 ± 0.15 | 1.21 ± 0.04 |

TABLE 7-continued

Summary of Effect of Herbal Extract on Follicle Stimulating Hormone (FSH), Lutenizing Hormone (LH), Progesteron, Estrogen and Testosterone in Rats

| Group | FSH (mIU/ml) | LH (mIU/ml) | Progesterone (ng/ml) | Estrogen (pg/ml) | Testosterone (ng/ml) |
|---|---|---|---|---|---|
| Group 4 Mid dose 300 mg/kg | 4.87 ± 0.20 | 4.36 ± 0.20 | 1.96 ± 0.09 | 10.18 ± 0.28 | 1.31 ± 0.03 |
| Group 5 High dose 500 mg/kg | 4.25 ± 0.22*** | 4.07 ± 0.12 | 2.48 ± 0.08* | 11.02 ± 0.13* | 1.83 ± 0.03 |
| Group 6 Positive control | 3.96 ± 0.22*** | 3.76 ± 0.11** | 3.31 ± 0.15*** | 12.35 ± 0.25*** | 13.01 ± 0.41*** |

$P < 0.05$,
$P < 0.01$ and
$P < 0.001$ vs. Group 1;
*$P < 0.05$,
**$P < 0.01$ and
***$P < 0.001$ vs. Group 2.

Follicle Stimulating Hormone (FSH)

Referring to Table 7, the serum FSH level significantly increased in negative control ($P<0.001$, 5.70±0.33) when compared to sham control and significantly decreased in *Eurycoma longifolia* aqueous extract high dose ($P<0.001$, 4.25±0.22) treated group and positive control group ($P<0.001$, 3.96±0.22) as compared to negative control.

FSH levels were elevated in ovariectomized rats. The changes of serum hormone in ovariectomized rats were similar to that in postmenopausal women.

Luteinizing Hormone (LH)

The results in Table 7 showed significantly elevated ($P<0.001$, 4.69±0.22) serum LH levels in negative control group, when compared to sham control. It significantly decreased ($P<0.001$, 3.76±0.11) in positive control group as compared to negative control. We observed decrease in the level of serum LH in *Eurycoma longifolia* aqueous extract high dose treated groups when compared to negative control.

Gonadotropin releasing hormone produced by neuron that is found mainly in the hypothalamus and constitute common pathway to control LH and FSH and these secretions are controlled by neurotransmitter. Ovariectomy cause significant elevation in serum LH and FSH, oral administration of herbal extract promote estrogen release and diminishing the ascending FSH and LH in ovariectomized rats. The *Eurycoma longifolia* aqueous extract played protective role in deterious changes in aspects of postmenopausal associated hypothalamus pituitary ovarian hormones and thus shifting more physiologically balance.

Progesterone

Referring to Table 7, the serum progesterone level significantly decreased ($P<0.001$, 1.82±0.09) in negative control group as compared to sham control. It significantly increased in positive control ($P<0.001$, 3.31±0.15) and herbal extract high dose treated group ($P<0.05$, 2.48±0.08) when compared to negative control group.

Testosterone

The results in Table 7 showed significant decrease ($P<0.001$, 1.22±0.06) of serum testosterone level in negative control group when compared to sham control, and significant increase ($P<0.001$, 13.01±0.41) in positive control group when compared to negative control group. Increasing trend was seen in treatment group in dose dependent manner.

The *Eurycoma longifolia* aqueous extract treated groups were observed to increase serum testosterone levels when compared to negative control group.

Estrogen

Still referring to Table 7, the estrogen levels significantly decreased ($P<0.00$, 9.49±0.27) in negative control group when compared to sham control. It significantly increased ($P<0.001$, 12.35±0.25) in positive control group when compared to negative control group and *Eurycoma longifolia* aqueous extract high dose treated groups showed significant increase ($P<0.001$) in the levels of estrogen when compared to negative group.

The results of the present study showed that both serum estrogen and testosterone concentration decreased when the rats were ovariectomized. Serum testosterone level reduced quickly in ovariectomized rats. This suggests that most serum testosterone is synthesized from the ovaries.

(v) Organ Weight

The mean uterus weight was significantly decreased in ovariectomized control and administration of *Eurycoma longifolia* aqueous extract and testosterone undecanoate after ovariectomy prevented the ovariectomy induced loss of uterus weight.

As represented in Table 8, uterine weight of negative control group significantly decreased ($P<0.001$, 238.81±5.39) when compared to sham control group. The positive control group showed significant increase ($P<0.001$, 389.74±8.26) uterine weight when compared to negative control group. Increasing trend was seen in treatment group in dose dependent manner.

TABLE 8

Summary of Effect of Herbal Extract on Rat Uterus Weight
UTERUS WEIGHT (mg)

| Group 1 | Group 2 | Group 3 | Group 4 | Group 5 | Group 6 |
|---|---|---|---|---|---|
| 679.06 ± 6.65 | 238.81 ± 5.39### | 235.84 ± 4.03 | 240.73 ± 2.93 | 256.39 ± 4.41 | 389.74 ± 8.26*** |

$p < 0.001$ vs. Group 1;
*** $p < 0.001$ vs. Group 2.

A marked atrophy of the uterus has been used as evidence of the success of ovariectomy, uterine weight constitute a typical marker for estrogenic action. Estrogen plays a predominant role in reducing uterine weight gain. The ovariectomy caused reduction in estrogen hormone which accordingly caused a reduction in uterine estrogen receptors. This may produce decrease in the proliferative layers, luminal epithelium, thin stroma and myometrium which accordingly reduces uterus weight.

CONCLUSION

The present results support the use of *Eurycoma longifolia* aqueous extract as promising pharmacological agent for the alleviation or treatment of symptoms and/or conditions associated to hormonal imbalance in females, including menopause and its related symptoms, in women having such symptoms, in place of replacement of hormone therapy. On the findings of the present study, it can be concluded that the extract could be used to treat the symptoms and/or conditions associated to hormonal imbalance and menopause in females. Further the herbal extract at higher dose exhibited better response and overall improvement seen in dose depending manner.

What is claimed is:

1. A method for the treatment or alleviation of symptoms or conditions associated to hormonal imbalance in females caused by peri-menopause, menopause and/or post-menopause and its related symptoms, the method comprising the step of administering to a subject in need thereof a composition having a therapeutically effective amount of an extract derived from *Eurycoma longifolia*.

2. The method according to claim 1, wherein the composition comprises an aqueous extract of *Eurycoma longifolia*.

3. The method according to claim 1, wherein the therapeutically effective amount of the extract is in a range of 10 mg to 1000 mg.

4. The method according to claim 1, wherein the therapeutically effective amount of the extract is in a range of 50 mg to 500 mg.

5. The method according to claim 1, wherein the composition further comprises a pharmaceutically acceptable carrier.

6. The method according to claim 1, wherein the treatment or alleviation of symptoms or conditions associated to hormonal imbalance caused by peri-menopause, menopause and/or post-menopause and its related symptoms, is by way of inducing a change of one or more of estrogen, progesterone, follicle stimulating hormone (FSH) and luteinizing hormone (LH) content in the blood.

7. The method according to claim 1, wherein the treatment or alleviation of symptoms or conditions associated to hormonal imbalance caused by peri-menopause, menopause and/or post-menopause and its related symptoms, is by way of normalizing one or more of the content of estrogen, progesterone, follicle stimulating hormone (FSH) and luteinizing hormone (LH) in the blood, by:
   increasing serum estrogen level by 0.3% to 16.0%,
   increasing serum progesterone level by 3.0% to 37.0%,
   decreasing serum follicle stimulating hormone (FSH) level by 7% to 26.0%,
   decreasing serum luteinizing hormone (LH) level by 2.0% to 14.0%.

8. The method according to claim 1, wherein the symptoms or conditions associated to hormonal imbalance caused by peri-menopause, menopause and/or post-menopause and its related symptoms, comprise lowered production of the female sex hormones estrogen and progesterone.

9. The method according to claim 1, wherein the symptoms or conditions associated to hormonal imbalance caused by peri-menopause, menopause and/or post-menopause and its related symptoms, are one or more of:
   physical symptoms comprising hot flashes, sweating, and secondary vasomotor instability;
   psychological and emotional symptoms comprising fatigue, irritability, insomnia, inability to concentrate, depression, memory loss, headache, anxiety, nervousness, reduced fertility, and reduced sexual desire;
   additional physical symptoms comprising intermittent dizziness, paresthesias, palpitations, tachycardia, nausea, constipation, diarrhea, arthralgia, myalgia, cold hands and feet, and weight gain;
   changes to the genitals;
   urinary incontinence;
   vaginal dryness;
   loss of pelvic muscle tone;
   increased risk of cardiovascular disease; and
   osteoporosis.

* * * * *